April 13, 1971 S. R. SMITH Plant Pat. 3,041
AZALEA PLANT
Filed May 7, 1969
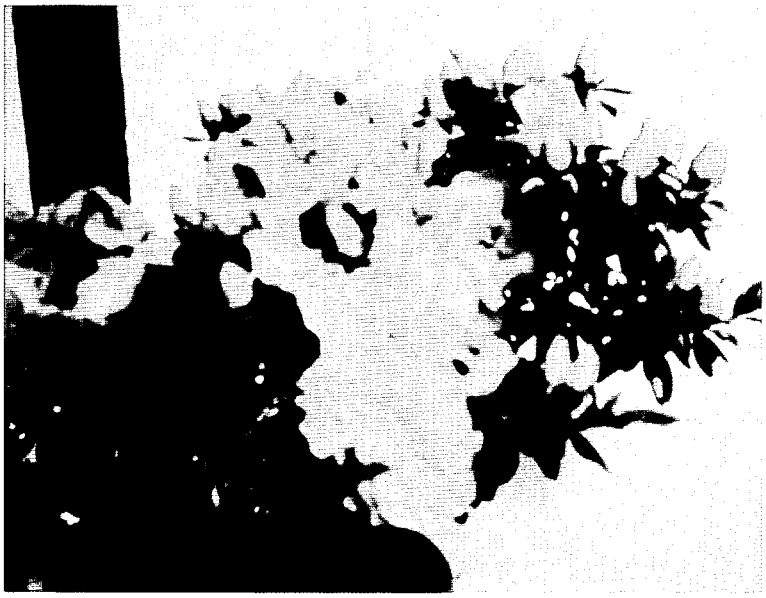
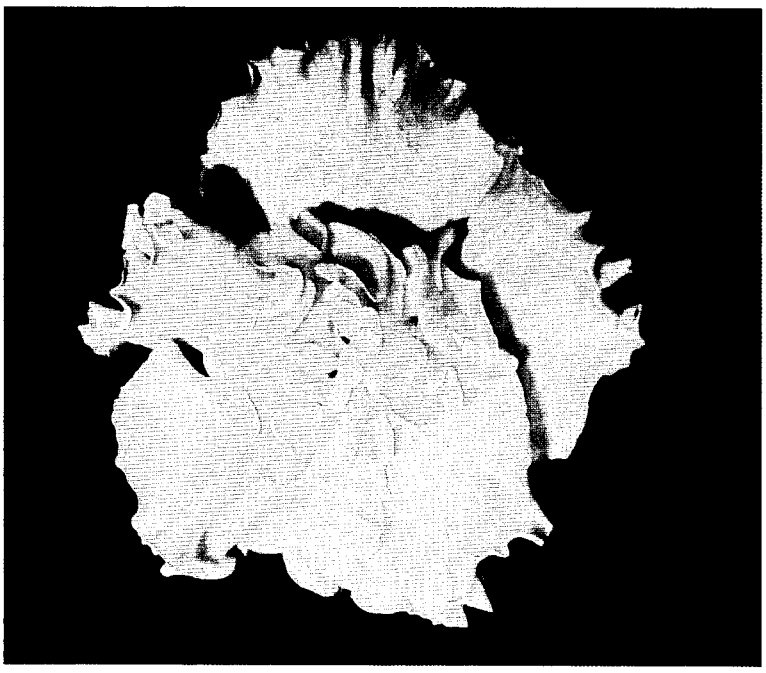
Inventor.
Spencer R. Smith
By: Robb & Robb
Attorneys.

United States Patent Office

Plant Pat. 3,041

Patented Apr. 13, 1971

3,041

AZALEA PLANT

Spencer R. Smith, Rockwood, Mich., assignor to Post Gardens, Inc., Rockwood, Mich.

Filed May 7, 1969, Ser. No. 822,749

Int. Cl. A01h *5/12*

U.S. Cl. Plt.—57 1 Claim

The present invention relates to a new and distinct variety of azalea plant which was discovered by me as a sport of the azalea variety known as "Chimes" (unpatented).

At the time of my discovery aforesaid, a large block of plants of the variety "Chimes" were being grown commercially under my direction and management in the nursery of my assignee, located at Rockwood, Mich. While tending these plants, my attention was attracted to one particular plant on which there was one stem which bore flowers of extra large size, with ruffled edges, and having an outstanding glowing or iridescent pink color. Upon close inspection of this plant, I found that it had sported, and I thereupon took immediate steps to carefully preserve the sport and keep it under close observation. Shortly after my discovery, I also took steps to asexually reproduce the sport, as performed by propagating cuttings taken by me therefrom and planted in the nursery aforesaid at Rockwood, Mich. Continued observations and tests of the sport and the progeny thereof derived from the aforementioned cuttings have convinced me that the unusual features thereof, as initially observed, together with other distinctive features subsequently noted, are fixed and established and come true to form, and that my new azalea variety represents a commercially valuable variety that is definitely distinguished from its parent, as well as from all other azalea varieties known to me, as evidenced by the following unique combination of characteristics which are outstanding therein:

(1) A bushy and medium vigorous plant habit;
(2) Heavier and stronger stems than those of the parent variety "Chimes";
(3) Attractive, dark glossy green foliage which is somewhat darker, heavier, thicker and more oval in shape than the foliage of "Chimes";
(4) A profuse and uniform blooming habit when grown in the greenhouse;
(5) An exceptionally large bloom size ranging from 4 to 5 inches as compared to the average 2 to 3 inch bloom size of "Chimes";
(6) A distinctive and attractive bloom shape which is more flat than in "Chimes," with the blooms having ruffled edges and raised, semi-double centers;
(7) A distinctive and attractive iridescent pink bloom color which is brighter and more glowing than the bloom color of "Chimes"; and
(8) Good lasting qualities of both foliage and blooms.

The accompanying drawing shows a typical specimen plant and a specimen single bloom of my new azalea variety as depicted in color as nearly true as it is reasonably possible to make the same in a color illustration of this character.

The following is a detailed description of the new variety, with color terminology in accordance with Koster's Color Guide, except where general color terms of ordinary dictionary significance are obvious:

Locality where grown and observed: Rockwood, Mich.
Parentage: Sport of "Chimes."
Propogation: Holds its distinguishing characteristics through succeeding propagations by cuttings.

*Plant*

Form: Bush.

Habit: Medium vigorous.
Rooting: Coordinate.
Blooming habit: Profuse and uniform.
Blooming season: From January to April, in greenhouse.
Suitability for forcing: Excellent.
Foliage:
*Size.*—Medium.
*Quantity.*—Normal.
*Color.*—New foliage—Upper side—light green. Under side—lighter than upper side. Old foliage—Upper side—dark glossy green, corresponding to near Holly Green, Plate 82. Under side—Light green.
*Shape.*—Oval.
*Texture.*—Upper side—glossy. Under side—rough.
*Margin.*—Smooth.
*Aspect.*—Heavy and thick.
*Disease resistance.*—Similar to parent variety, as determined by comparison with parent and other varieties grown under the same conditions at Rockwood, Mich.

*Flowers*

Borne: Several in clusters; on strong, short stems.
Quantity of bloom: Abundant, in greenhouse.
Continuity: One season.
Permanence: From 3 to 4 weeks.
Petalage:
*Number of petals under normal conditions.*—From 5 to 7, with many small petals in a raised center cluster.
*Color.*—Bright neon or glowing pink, corresponding to near Crimson Carmine, Plate 41.
*Texture.*—Durable and of good substance.
*Shape.*—Round, with serrated edges giving a ruffled appearance.
*Arrangement.*—Overlapping.

*Reproductive organs*

Stamens: Number—6. Color—reddish brown.
Pollen: Color—reddish brown.
Styles: Color—red.
Ovaries: 5 in number.

*General observations*

To the best of my knowledge, my new azalea bears the largest flowers of any azalea varieties in commercial production today. The large flower size, ruffled flower edges and bright glowing pink color make the flowers very impressive and enhance the commercial value of the new variety.

I claim:

1. A new and distinct variety of azalea plant, substantially as herein shown and described, characterized particularly as to novelty by the unique combination of a bushy and medium vigorous plant habit, heavier and stronger stems than those of the parent variety "Chimes," attractive, dark glossy green foliage which is somewhat darker, heavier, thicker and more oval in shape than the foliage of "Chimes," a profuse and uniform blooming habit when grown in the greenhouse, an exceptionally large bloom size ranging from 4 to 5 inches as compared to the average 2 to 3 inch bloom size of "Chimes," a distinctive and attractive bloom shape which is more flat than in "Chimes," with the blooms having ruffled edges and raised, semi-double centers, a distinctive and attractive iridescent pink bloom color which is brighter and more glowing than the bloom color of "Chimes," and good lasting qualities of both foliage and blooms.

No references cited.

ROBERT E. BAGWILL, Examiner